United States Patent
Mach et al.

(10) Patent No.: US 11,298,001 B2
(45) Date of Patent: Apr. 12, 2022

(54) CALIBRATION TOOL FOR ROTATING ENDOSCOPE

(71) Applicant: Canon USA Inc., Melville, NY (US)

(72) Inventors: Anderson Thi Mach, Cambridge, MA (US); Tzu-Yu Wu, Malden, MA (US); Jacob Schieffelin Brauer, Cambridge, MA (US)

(73) Assignee: Canon U.S.A., Inc., Melville, NY (US)

( * ) Notice: Subject to any disclaimer, the term of this patent is extended or adjusted under 35 U.S.C. 154(b) by 419 days.

(21) Appl. No.: 16/362,351

(22) Filed: Mar. 22, 2019

(65) Prior Publication Data
US 2019/0298154 A1  Oct. 3, 2019

Related U.S. Application Data

(60) Provisional application No. 62/650,155, filed on Mar. 29, 2018.

(51) Int. Cl.
*A61B 1/00* (2006.01)
*G06T 7/80* (2017.01)

(52) U.S. Cl.
CPC ...... *A61B 1/00057* (2013.01); *A61B 1/00096* (2013.01); *A61B 1/00172* (2013.01); *G06T 7/80* (2017.01); *A61B 1/0014* (2013.01); *A61B 1/00137* (2013.01); *G06T 2207/10068* (2013.01)

(58) Field of Classification Search
CPC ............ A61B 1/00057; A61B 1/00135; A61B 1/00137; A61B 1/0014; A61B 1/00172; A61B 1/00096; G06T 7/80; G06T 2207/10068
See application file for complete search history.

(56) References Cited

U.S. PATENT DOCUMENTS

| | | | | |
|---|---|---|---|---|
| 5,142,359 A * | 8/1992 | Yamamori | ......... | A61B 1/00057 348/175 |
| 5,820,547 A * | 10/1998 | Strobl | ................ | A61B 1/00057 600/127 |
| 6,361,490 B1 * | 3/2002 | Irion | .................... | A61B 5/0059 434/267 |
| 6,537,207 B1 * | 3/2003 | Rice | .................. | A61B 1/00142 600/121 |

(Continued)

FOREIGN PATENT DOCUMENTS

| | | |
|---|---|---|
| JP | 2010-515947 A | 5/2010 |
| JP | 2011110157 A | 6/2011 |
| WO | 2017/117203 A1 | 7/2017 |

OTHER PUBLICATIONS

Web, Reveal Distal Attachment Cap, US Endoscopy, 3 pages, http://www.usendoscopy.com/Products/Reveal-distal-attachment-cap.aspx.

(Continued)

*Primary Examiner* — John P Leubecker
(74) *Attorney, Agent, or Firm* — Canon U.S.A., Inc. IP Division

(57) ABSTRACT

Apparatus and methods for correcting distortion of a spectrally encoded endoscopy ("SEE"), more specifically, the subject disclosure provides a calibration tool calibrating a rotating spectrally encoded endoscope, which may be reused to recalibrate the endoscope throughout the lifecycle, and which may further act to protect the endoscope during packaging, shipping and handling.

9 Claims, 8 Drawing Sheets

(56) References Cited

U.S. PATENT DOCUMENTS

| | | | |
|---|---|---|---|
| 7,170,677 B1* | 1/2007 | Bendall | A61B 1/0005 |
| | | | 348/49 |
| 8,382,657 B1* | 2/2013 | Bodor | A61B 1/00057 |
| | | | 600/101 |
| 8,913,114 B2 | 12/2014 | Yoshino | |
| 9,017,248 B2 | 4/2015 | Gono | |
| 9,066,651 B2 | 6/2015 | Johnston | |
| 2001/0051761 A1* | 12/2001 | Khadem | A61B 1/00057 |
| | | | 600/117 |
| 2002/0077677 A1* | 6/2002 | Beck | A61B 5/0059 |
| | | | 607/88 |
| 2009/0221872 A1* | 9/2009 | Liddle | A61B 1/00057 |
| | | | 600/121 |
| 2009/0237498 A1 | 9/2009 | Modell et al. | |
| 2011/0069162 A1* | 3/2011 | Ozawa | A61B 1/00057 |
| | | | 348/68 |
| 2011/0140003 A1* | 6/2011 | Beck | A61B 1/00057 |
| | | | 250/459.1 |
| 2011/0149057 A1* | 6/2011 | Beck | G01N 21/6456 |
| | | | 348/65 |
| 2012/0281211 A1* | 11/2012 | Murugkar | A61B 1/00172 |
| | | | 356/301 |
| 2013/0208106 A1* | 8/2013 | De Braak | G01M 11/0264 |
| | | | 348/130 |
| 2014/0022365 A1* | 1/2014 | Yoshino | A61B 1/00096 |
| | | | 348/65 |
| 2014/0246563 A1* | 9/2014 | McCaffrey | A61B 1/00057 |
| | | | 250/208.1 |
| 2014/0267656 A1 | 9/2014 | Blanquart | |
| 2015/0018645 A1 | 1/2015 | Farkas et al. | |
| 2016/0015247 A1* | 1/2016 | Irion | A61B 1/00057 |
| | | | 356/432 |
| 2016/0048953 A1* | 2/2016 | Zhao | G01D 1/00 |
| | | | 382/103 |
| 2017/0035424 A1 | 2/2017 | Binmoeller | |
| 2018/0007346 A1* | 1/2018 | Ushijima | A61B 1/00039 |
| 2018/0024349 A1* | 1/2018 | Nagamizu | H04N 17/002 |
| | | | 348/68 |
| 2018/0120212 A1* | 5/2018 | Hosoda | A61B 1/07 |
| 2019/0028614 A1* | 1/2019 | De Paepe | H04N 1/6008 |

OTHER PUBLICATIONS

Wenbo Wang, et al., Disposable sheath that facilitates endoscopic Raman spectroscopy, Web, Journal of Biomedical Optics, vol. 21, Issue 2, http://biomedicaloptics.spiedigitallibrary.org/article.aspx?articleid=2488934, Feb. 17, 2017.

Joshua Gafford, et al., Snap-On Robotic Wrist Module for Enhanced Dexterity in Endoscopic Surgery, May 16, 2016, pp. 1-8, 2016 IEEE International Conference on Robotics and Automation (ICRA), May 16-21, 2016, IEEE, Stockholm, Sweden.

\* cited by examiner

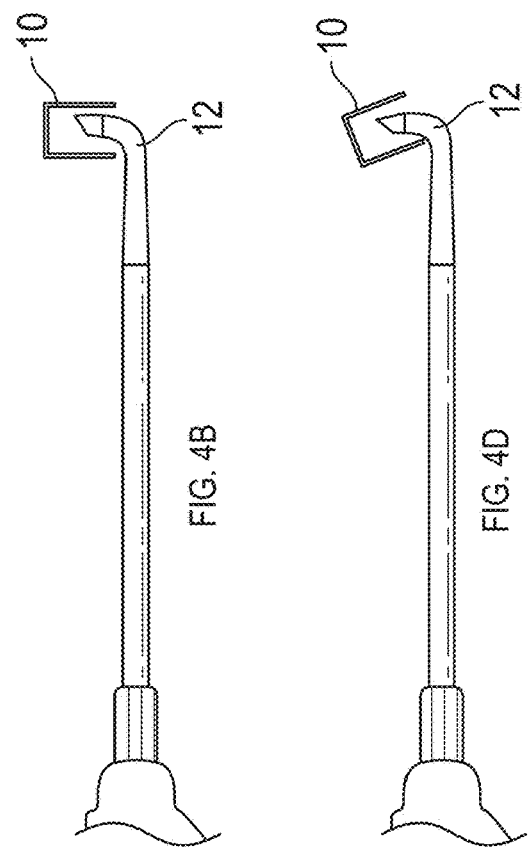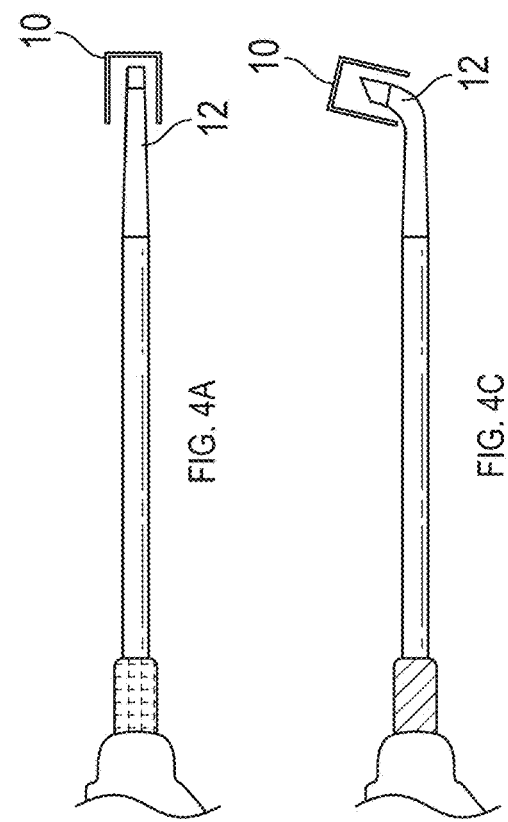

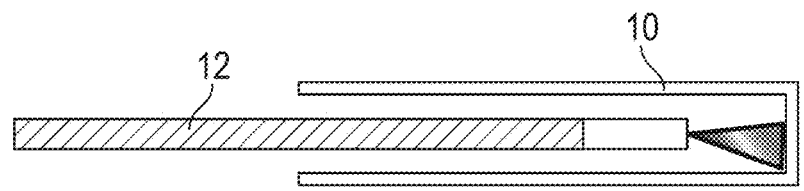
FIG. 9A
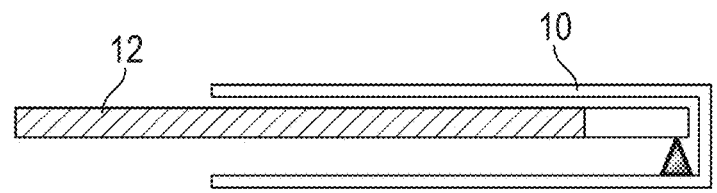
FIG. 9B
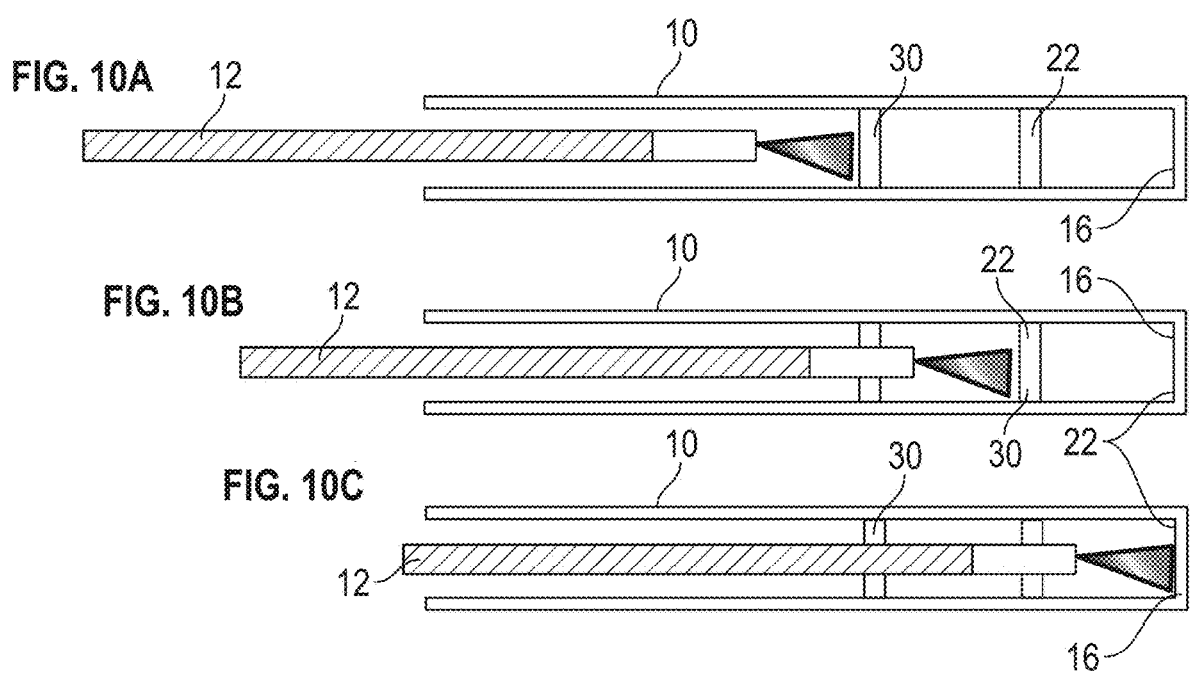
FIG. 10A
FIG. 10B
FIG. 10C

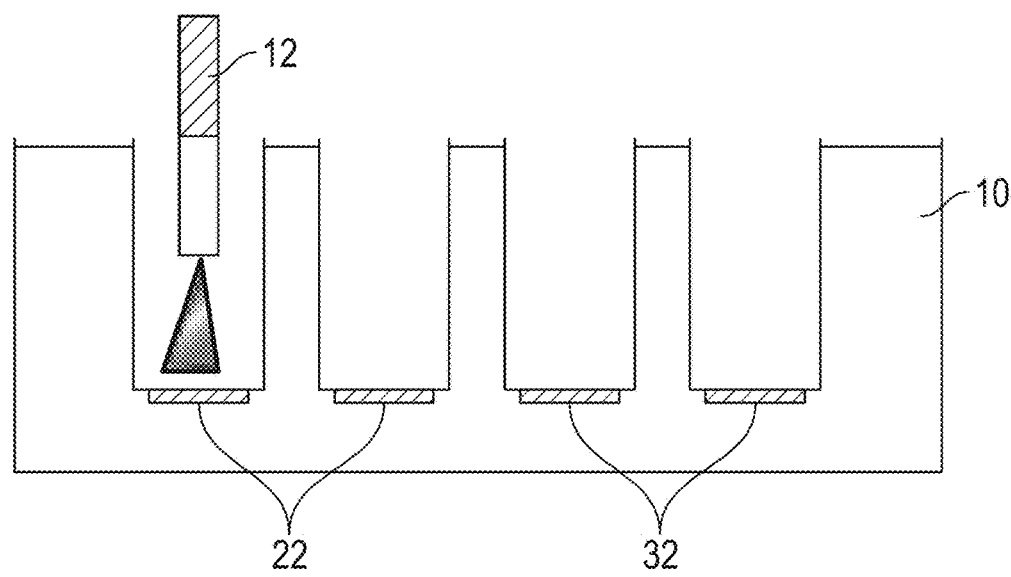
FIG. 11
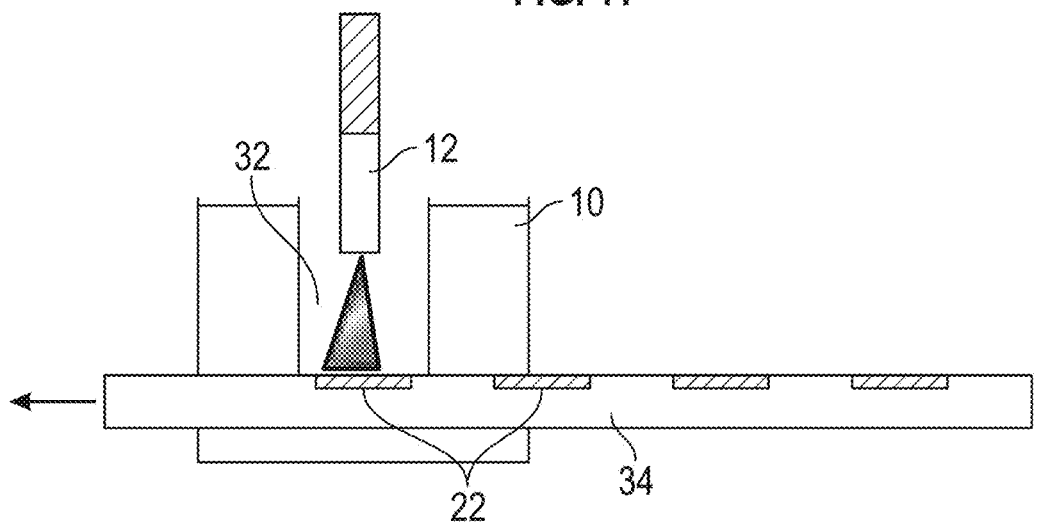
FIG. 12
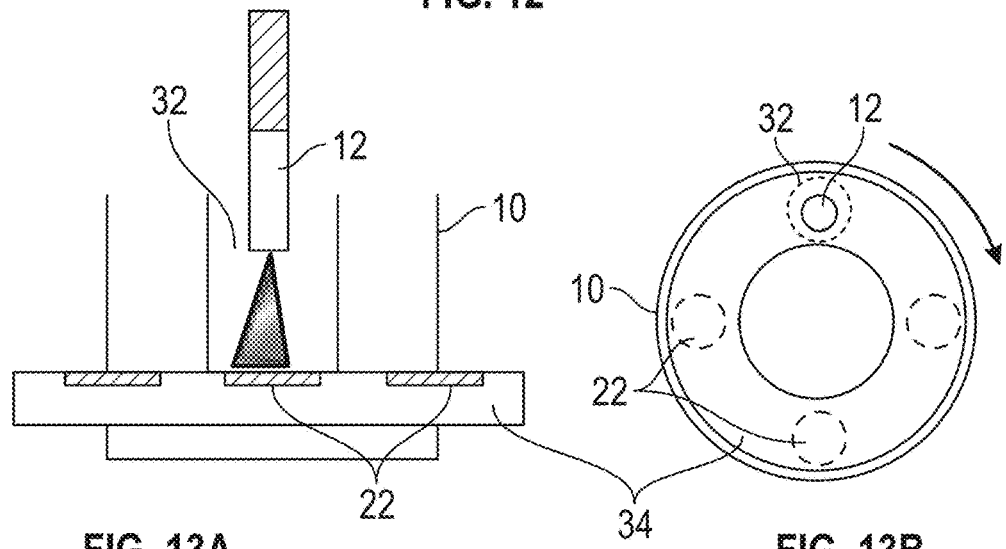 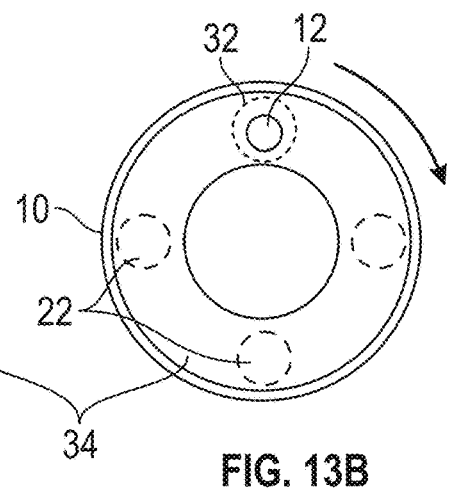
FIG. 13A   FIG. 13B

CALIBRATION TOOL FOR ROTATING ENDOSCOPE

CROSS REFERENCE TO RELATED PATENT APPLICATIONS

This application claims priority from U.S. Provisional Patent Application No. 62/650,155 filed on Mar. 29, 2018, in the United States Patent and Trademark Office, the disclosure of which is incorporated by reference herein in its entirety.

FIELD OF THE DISCLOSURE

The present disclosure relates generally to apparatus and methods for calibrating a scanning electron endoscope ("SEE"), and more particularly, to calibrating a rotating SEE.

BACKGROUND OF THE DISCLOSURE

Medical probes have the ability to provide images from inside a patient's body. Considering the potential harm capable to the human body caused by the insertion of a foreign object, it is preferable that the probe be as small as possible. Additionally, the ability to provide images within small pathways such as vessels, ducts, incisions, gaps and cavities dictates the use of a small probe One particularly useful medical probe is the SEE, which is a miniature endoscope that can conduct high-definition imaging through a sub-mm diameter probe. In operation, light from a light guiding component found in the SEE probe, (single mode fiber ("SMF") usually for better resolution) is first coupled into a coreless fiber and then into a Gradient Index ("GRIN") lens and then the light is diffracted through a prism with a grating. The diffracted light is scanned across the sample to be analyzed. Light reflected by the sample is captured by a detection fiber and imaged for viewing.

As an example of a calibration technique for an endoscope that scans an optical fiber and acquires an image, Japanese Patent Application Laid-Open Publication No. 2010-515947 discloses a scanning beam apparatus. The Japanese Patent above discloses a method for calibrating a scanning beam apparatus, the method including acquiring an image of a calibration pattern using the scanning beam apparatus, comparing the acquired image with a representation of the calibration pattern and calibrating the scanning beam apparatus based on the comparison, in order to improve distortion of the acquired image by enhancing the accuracy of estimation of the position of an illumination spot for each pixel point in a scan pattern.

In recent years SEE have advanced to allow for a greater field of vision for the endoscope, while retaining the diminutive size leading to less evasive imaging and surgical procedures. As provided in WO publication No. 2017/117203, the use of a rotating light dispersion fiber in the SEE allows for varying angles of incidents of light from the light dispersion fiber, which relays to a greater field of vision captured by the detection fiber.

Specifically, the polychromatic light emanating from this rotating SEE probe is spectrally dispersed and projected in such a way that each color (wavelength) illuminates a different location on the tissue along the dispersive line. Reflected light from the tissue can be collected and decoded by a spectrometer to form a line of image, with each pixel of the line image corresponding to the specific wavelength of illumination. Spatial information in the other dimension perpendicular to the dispersive line is obtained by rotating the light dispersion fiber using a motor. For the forward viewing SEE imaging, spatial information in the other dimension perpendicular to the dispersive line is obtained by rotating the probe using a rotary motor such that target is circularly scanned.

Due to various environmental variables, manufacturing variables, imperfect electronics, the sensitivity of the scanning fiber apparatus, and/or other factors, calibration of a SEE is typically required for improved and/or consistent imaging. The added complications of having a rotating probe, as provided in WO publication No. 2017/117203, further calls for calibration and method intended for a rotating SEE.

SUMMARY

The subject disclosure provides apparatus and methods for correcting distortion of a rotating spectrally encoded endoscopy image. More specifically, the subject disclosure provides an apparatus for calibrating a scanning electron endoscope ("SEE"), the apparatus comprising a body configured to encompass at least a portion of a SEE, as well as a bottomed surface affixed to a distal end of the body; and a calibration chart configured on an inside wall portion of the apparatus, wherein the apparatus has an open end, opposite the bottomed surface, wherein the open end is configured to receive the at least a portion of the SEE, and the SEE is a rotating SEE.

In various embodiments, the apparatus further comprising an attachment element configured to rigidly and removably attach the apparatus to the SEE. Furthermore, the apparatus is configured wherein the body of the apparatus is configured to further extend onto a sheath of the SEE.

In another embodiment, the apparatus is configured for repeated attachment and removal from the at least a portion of the SEE.

In further embodiments of the apparatus, the calibration chart is positioned at a predetermined distance from the SEE.

In yet another embodiment, the apparatus has the bottomed surface configured to be ruptured by the SEE, allowing the SEE to protrude through the bottomed surface of the apparatus. In further embodiment, the inside wall portion may be an inside wall portion of the bottomed surface. Furthermore, the inside wall portion may be an inside wall portion of the body.

In other embodiment of the subject apparatus, a second calibration chart configured on an inside wall portion of the apparatus is utilized.

Further embodiment devise the bottomed surface to be configured to be rotatable or pivotable, allowing for rearrangement of the bottomed surface with respect to the SEE.

In additional embodiment, the apparatus further comprising an intermediate surface configured in the apparatus, wherein the intermediate surface contains at least one calibration chart.

The subject innovation further details a method for calibrating a rotating SEE, the method comprising: providing a calibration apparatus comprising: a body configured to encompass at least a portion of a SEE; a bottomed surface affixed to a distal end of the body; and a calibration chart configured on an inside wall portion of the apparatus, wherein the apparatus has an open end, opposite the bottomed surface, wherein the open end is configured to receive the at least a portion of the SEE, and the SEE is a rotating SEE, the method including: scanning the calibration chart with an SEE spectral line to obtain an image; determining a sign of a tangential shift of the spectral line based on a slope of at least one of the radial lines of the first image in a polar coordinate; computing a magnitude of the tangential shift based on at least one of the radial lines of the first image in either a polar coordinate or a Cartesian coordinate; determining a sign of a radial shift of the spectral line based on whether the slope has a turning point or not; computing a magnitude of the radial shift by measuring a location of the turning point if the radial shift is determined to be negative; scanning the calibration chart with the SEE spectral line to obtain a second image if the radial shift is determined to be positive; computing the magnitude of the radial shift based on the magnitude of the tangential shift and a radius of the circle; and applying the tangential shift and the radial shift for a corrected calibration.

In various embodiment, the subject method further provides, wherein the calibration apparatus further comprising an attachment element configured to rigidly and removably attach the apparatus to the SEE.

In yet additional embodiment, the subject method teaches the calibration apparatus to be configured to further extend onto a sheath of the SEE.

BRIEF DESCRIPTION OF THE DRAWINGS

FIGS. 4A-4D provide various SEE probes fitted with exemplary calibration tools, according to one or more embodiment of the subject disclosure.

FIGS. 9(a) and 9(b) provide various SEE probes fitted with an exemplary calibration tool, according to one or more embodiment of the subject disclosure.

FIGS. 10(a)-10(c) provide an exemplary calibration tool, utilizing multiple stages of calibration, according to one or more embodiment of the subject disclosure.

FIG. 11 illustrates a SEE probes fitted with an exemplary calibration tool having multiple calibration wells, according to one or more embodiment of the subject disclosure.

FIG. 12 portrays a SEE probes fitted with an exemplary calibration tool having multiple calibration wells, according to one or more embodiment of the subject disclosure.

FIGS. 13A and 13B provide a SEE probes fitted with an exemplary calibration tool having multiple calibration wells, with 13A depicting a side view and 13B providing a top view, according to one or more embodiment of the subject disclosure.

In addition.

DETAILED DESCRIPTION

Further objects, features and advantages of the present disclosure will become apparent from the following detailed description when taken in conjunction with the accompanying figures showing illustrative embodiments of the present disclosure.

Figure 1A:
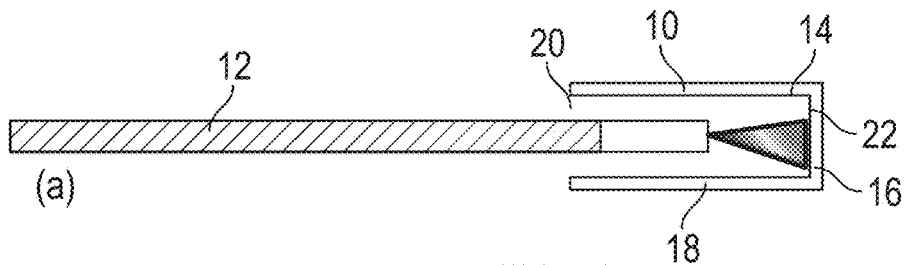
FIG. 1(a) provides an illustration of an exemplary SEE probe including a calibration tool, according to one or more embodiment of the subject disclosure.
Figure 1B:
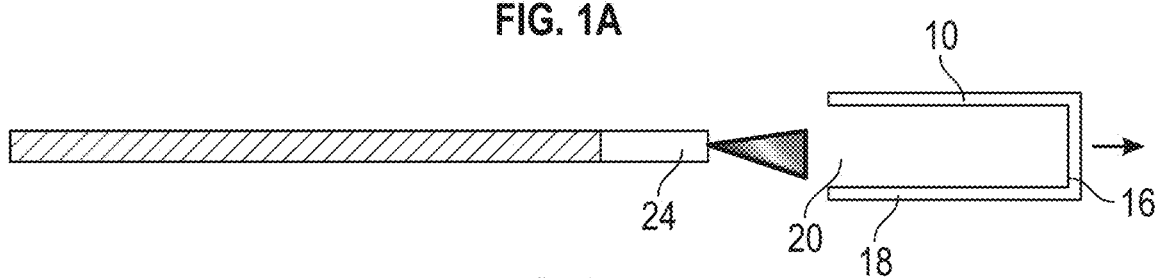
FIG. 1(b) provides an image of an exemplary SEE probe including a calibration tool being removed, according to one or more embodiment of the subject disclosure.

FIGS. 1(a) and 1(b) provide illustrations of an exemplary SEE probe including a calibration tool, according to one or more embodiment of the subject disclosure. In FIG. 1(a), the calibration tool 10 to configured to resemble a cylindrical cap, to be fitted to the SEE 12, while FIG. 1(b) depict the calibration tool 10 being removed from the SEE 12, preferably after calibration has been completed. The calibration tool 10 comprises a distal end 14, which has a bottomed cylindrical surface 16, and hollow cylindrical body 18 which is configured perpendicular to the bottomed cylindrical surface 16, and a proximal end 20 which is gapped for accepting the SEE 12. The bottomed cylindrical surface 16 is configured to accept a calibration chart 22, which is used for calibrating the SEE 12 (as detailed below). The calibration tool 10 is configured such that the inner calibration chart 22 is positioned at a predetermined distance with respect to the tip 24 of the SEE 12. The calibration is performed by irradiating light onto the calibration chart 22 and processing the image data of the inner surface of the cap. In various embodiments, an illumination source is configured to provide the irradiating light, with a detection fiber being incorporated to capture the reflected light and send the information to a spectrometer for processing the image data.

In various embodiments, the calibration tool 10 may be removable affixed to the SEE 12 by pressure fitment, snap fitment, rotationally coupled, clamped, buttoned, threaded, screwed, glued on, taped, or any other appropriate fastening means known in the art.

In addition, the calibration chart 22 may be configured to be water proof and/or solvent proof, allowing for cleaning and exposure of the calibration tool 10 to water and other elements.

The SEE 12 may be prepackaged with a calibration tool 10, for ease of operation and calibration. In this instance, the user may perform a re-calibration of the SEE 12 with the calibration tool 10 pre-fitted to the SEE 12. The user initiates the automatic calibration through the software which operates the SEE 12 within the calibration tool 10 (discussed in detail below). Upon completion of calibration, the user removes the calibration tool 10 and begins intended use of the SEE 12.

When the user is done operating the SEE 12, the user properly disposes of the SEE 12 and calibration tool 10. Alternatively, the SEE 12 may be recapped with the calibration tool 10 to enclose the SEE 12, which has been exposed to tissue or bodily fluids. Furthermore, and intended for non-disposable SEE's 12, the SEE 12 and calibration tool 10 may be re-sterilized individually, then the SEE 12 is re-capped with the calibration tool 10 and stored for future use.

Figure 2:
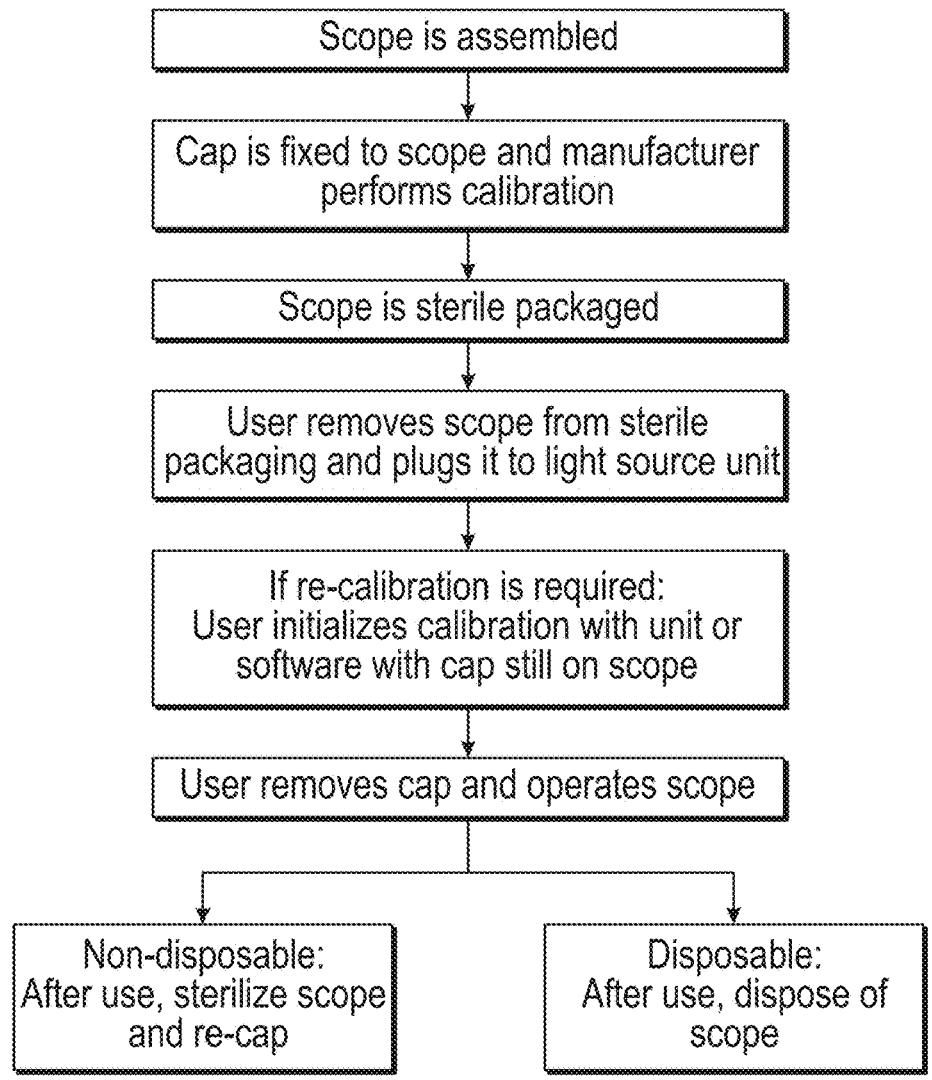
FIG. 2 is a flow chart illustrating a method for calibrating a SEE probe incorporating a calibration tool, according to one or more embodiment of the subject disclosure.

FIG. 2 is a flow chart illustrating a method for calibrating a SEE probe incorporating a calibration tool, according to one or more embodiment of the subject disclosure. As provided, the SEE 12 is assembled with the calibration tool 10 fixed to the SEE 12 by the manufacturer, and a manufacturer initiated calibration is performed. The SEE 12 and accompanying calibration tool 10 are sterile packed for shipment to an end user. The end user removes the combined SEE 12 and calibration tool 10 from the sterilized packaging, and recalibrates the SEE 12, which may have been unsettled during shipping and/or handling. After recalibration, the end user removes the calibration tool 10, and operates the SEE 12 as intended.

Figure 3A:
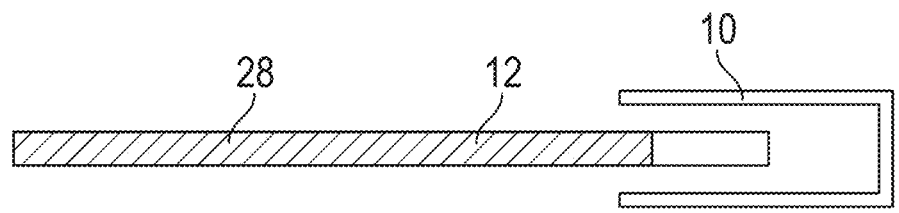
FIG. 3(a) depicts a SEE probe including an exemplary calibration tool, according to one or more embodiment of the subject disclosure.

FIG. 3(a) depicts a SEE probe including an exemplary calibration tool, according to one or more embodiment of the subject disclosure. In this embodiment, the SEE 12 may be covered by a rigid calibration tool 10, which would enhance protection of the SEE 12 tip 24. The calibration tool 10 may be attached to the SEE 12, at or near the proximal end of the SEE 12, as illustrated by the attachment element 26. The attachment element 26 or mechanical features of the calibration tool 10 may align the SEE 12 axially centered to the calibration chart 22, thus positioning the SEE 12 and calibration tool 10 for accurate and repeatable calibration. The rigid calibration tool 10 may also be useful in protecting the tip 24 in packaging, shipping, storage and/or handling of the SEE 12.

In addition, the calibration tool 10 may be utilized to prevent dust, particles, physical contamination from accumulating on the distal imaging lens of the SEE 12, or window of the SEE 12. If the SEE 12 scope is flexible, the calibration tool 10 can cover a length of the flexible sheath 28 to protect from bending or kinking as well (See FIG. 3(b)).

Figure 3B:
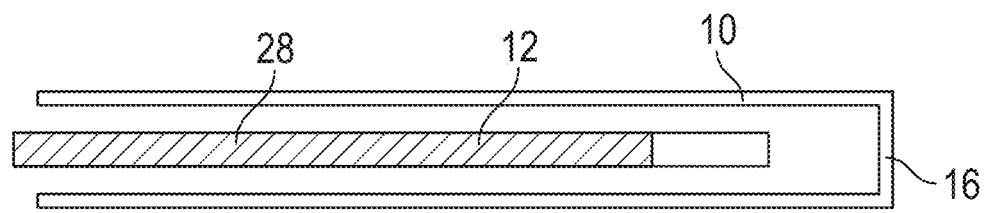
FIG. 3(b) portrays a SEE probe including an exemplary calibration tool, according to one or more embodiment of the subject disclosure.
Figure 3C:
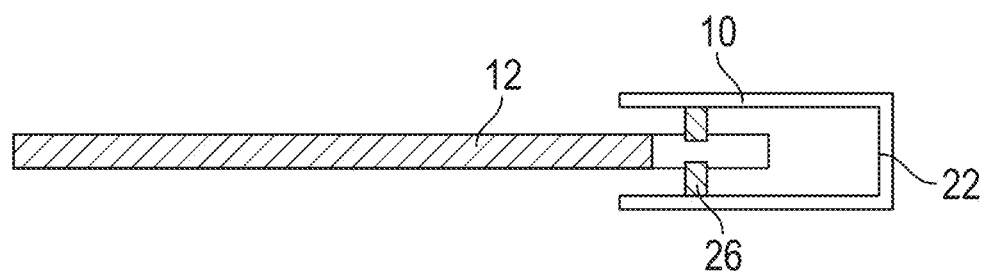
FIG. 3(c) illustrates a SEE probe including an exemplary calibration tool, according to one or more embodiment of the subject disclosure.
Figure 3D:
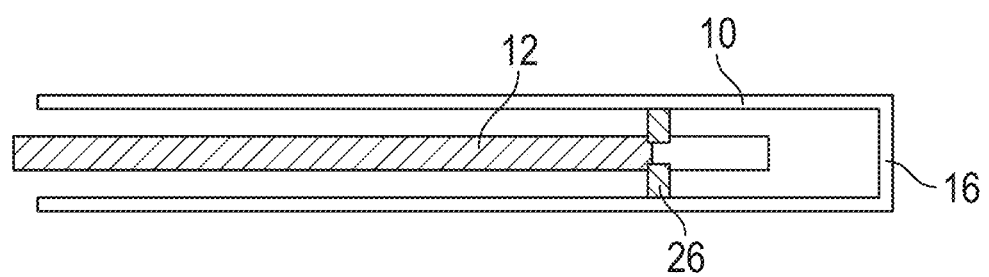
FIG. 3(d) portrays a SEE probe including an exemplary calibration tool, according to one or more embodiment of the subject disclosure.

FIGS. 3(a) through 3(d) portray a SEE probe including an exemplary calibration tool, according to one or more embodiment of the subject disclosure. FIGS. 3(a) and 3(c) incorporate a calibration tool 10 configured to cover a shorter portion of the SEE 12, with FIG. 3(c) employing the attachment element 26 designed to better protect the tip 24 of the SEE 12. FIGS. 3(b) and 3(d) detail a calibration tool 10 configured to cover a longer portion of the SEE 12, which may include the sheath 28 portion of the SEE 12 as well. The sheath 28, may be flexible or rigid, with the calibration tool 10 designed to offer greater protection to the sheath 28 in addition to the See 12 tip 24. FIG. 3(d) also employs the attachment element 26 designed to better protect the tip 24 and sheath 28 of the SEE 12.

FIG. 4 provides various SEE probes fitted with exemplary calibration tools, according to one or more embodiment of the subject disclosure. In various instances, the SEE 12 may be utilized as a sub-system of a larger medical device. As provided in FIG. 4, the SEE 12 tips 24 of these sub-systems may be fitted by the subject calibration tool 10, which would be fitted to the distal end of the SEE 12.

Figure 5A:
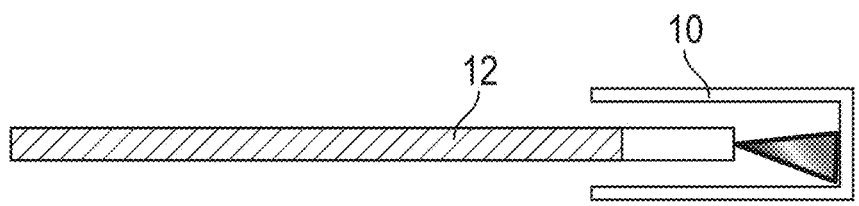
FIGS. 5(a) and 5(b) depict a SEE probe including an exemplary calibration tool, according to one or more embodiment of the subject disclosure.
Figure 5B:
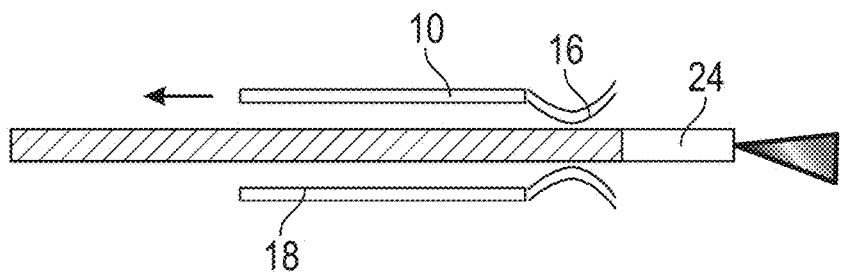

FIGS. 5(a) and 5(b) depict a SEE probe including an exemplary calibration tool having a break-through cylindrical surface 16, according to one or more embodiment of the subject disclosure. In this embodiment, the subject calibration tool 10 incorporates a break-through bottomed cylindrical surface 16, wherein the calibration chart 22 is also broken-through once the SEE 12 has been calibrated. As provided in FIG. 5(a), the calibration tool 10 is fitted to the SEE 12, and calibration is conducted. Once calibration is completed, the calibration tool 10 is forcibly urged parallel to and towards the SEE 12, thus rupturing the bottomed cylindrical surface 16, and exposing the SEE 12 tip 24 for use, as provided in FIG. 5(b). The calibration tool 10 in this embodiment is intended for one-time calibration use only.

Figure 6A:
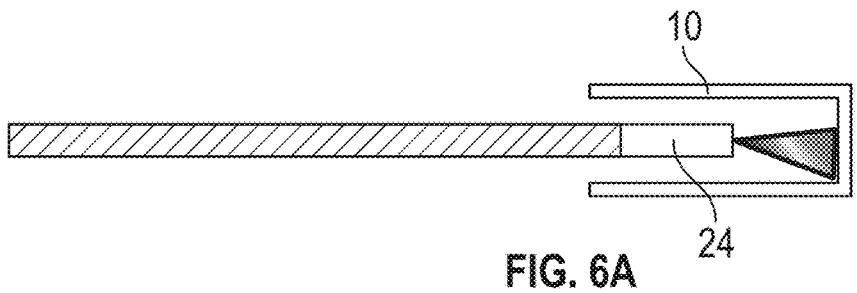
FIGS. 6(a)-6(c) provide an exemplary calibration tool, capable of removal and reassertion, according to one or more embodiment of the subject disclosure.
Figure 6B:
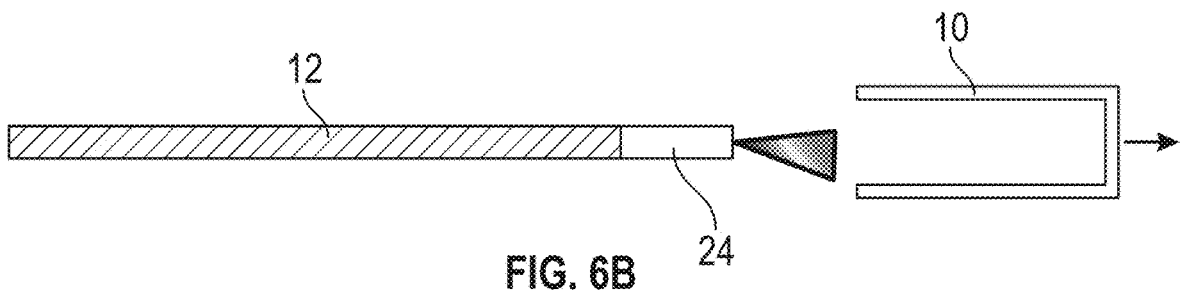
Figure 6C:
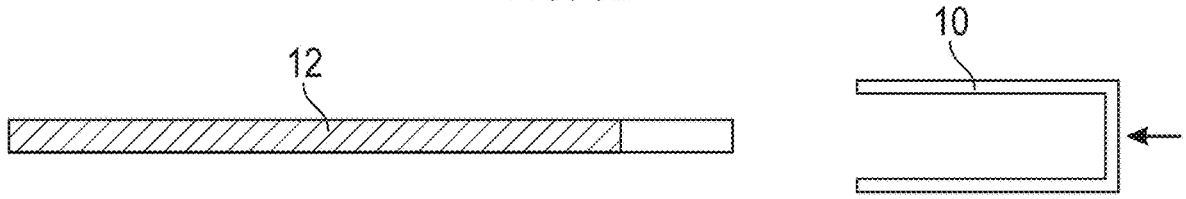

FIGS. 6(a)-6(c) provide an exemplary calibration tool, capable of removal and reassertion, according to one or more embodiment of the subject disclosure. In the embodiment provided in FIGS. 6(a) through 6(c), the calibration tool 10 is intended to be used repeatedly, as the calibration tool 10, may be removed and reasserted on the SEE 12. In this embodiment, the calibration tool 12 may be used as a safety device to cover the See 12 tip 24, after the tip 24 has been exposed to biological fluids and/or biological matter. In various other embodiments, the calibration tool 12 and SEE may both be sterilized, and the calibration tool 12 may be refitted on the SEE 12 for safe storage and future use. In an embodiment, the SEE may be designed for single use, such that after exposure to biological fluids, the SEE may be discarded. In such case, the SEE may also be recapped, thus ensuring the potentially biohazard material on the SEE is isolated for proper handling and disposal.

Figure 7A:
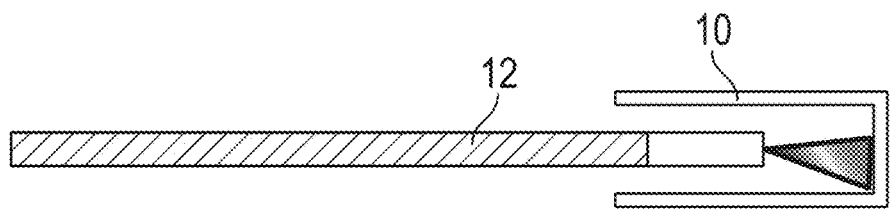
FIGS. 7(a) and 7(c) illustrate an exemplary calibration tool, according to one or more embodiment of the subject disclosure.
Figure 7B:
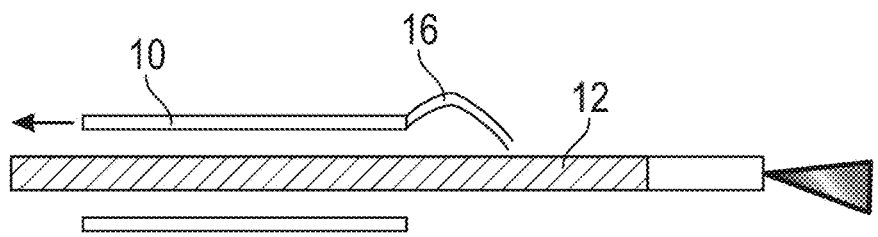
Figure 7C:
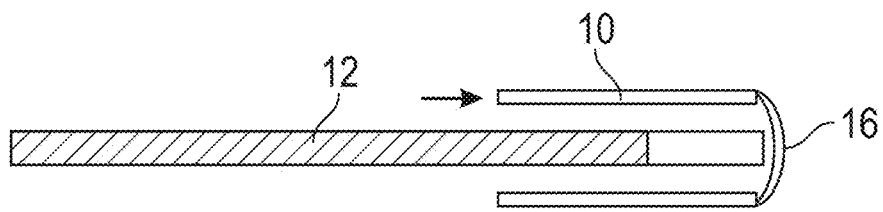
Figure 8A:
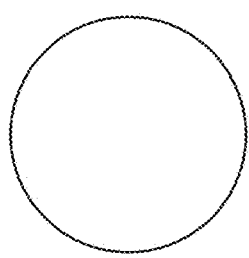
FIGS. 8(a) through 8(h) portrays various calibration charts, which may be utilized in an exemplary calibration tool, according to one or more embodiment of the subject disclosure.
Figure 8B:
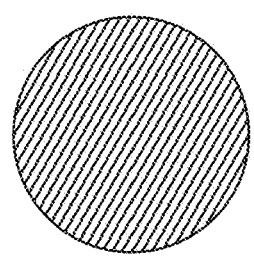
Figure 8C:
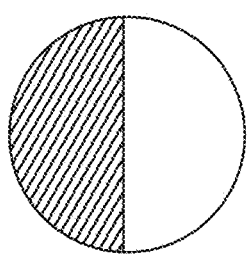
Figure 8D:
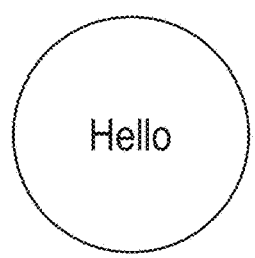
Figure 8E:
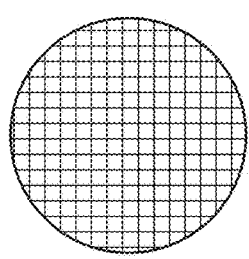
Figure 8F:
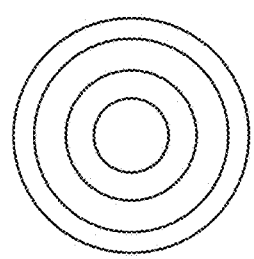
Figure 8G:
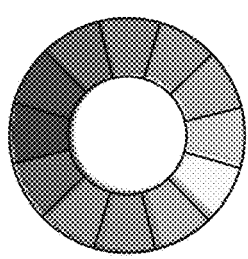
Figure 8H:
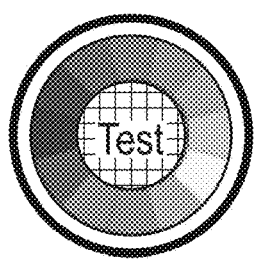

FIGS. 7(a) and 7(b) illustrate an exemplary calibration tool, according to one or more embodiment of the subject disclosure. In this embodiment, the calibration tool 10 is fitted with a bottomed cylindrical surface 16 capable of being rotated and/or pivoted. The rotating and/or pivoting is configured to allow the SEE 12 tip 24 to advance beyond and through the calibration tool 10, as seen in FIG. 7(b), without damaging the bottomed cylindrical surface 16 of the calibration tool 10, as well as the calibration chart 24. In various embodiments, the rotating and/or pivoting bottomed cylindrical surface 16 may consist of a shutter-type element, one or more pivot attachments, or derivatives thereof. As seen in FIGS. 7(a) through 7(c), calibration is accomplished with the calibration tool 10 configured on the SEE 12, wherein upon completion of calibration, the calibration tool 10 may be urged parallel to and towards the SEE 12, enacting the rotating and/or pivoting of the bottomed cylindrical surface 16, and exposing the SEE 12 tip 24 for use. Finally, FIG. 7(c) depicts how the calibration tool 10 may be returned to a position of protecting the tip 24, by urging the calibration tool 10 parallel to and away from the SEE 12, thus enacting the rotating and/or pivoting of the bottomed cylindrical surface 16 to conceal the SEE 12 and tip 24 from the environment.

In various embodiments, the rotating and/or pivoting bottomed cylindrical surface 16 may be configured for one-time use, wherein the bottomed cylindrical surface 16 is locked once the calibration tool 10 is urged parallel to and away from the SEE 12, thus enacting the rotating and/or pivoting of the bottomed cylindrical surface 16 to a concealed position. In another embodiment, the rotating and/or pivoting bottomed cylindrical surface 16 may be configured for repeated use, allowing an end user to repeatedly expose and conceal the tip 24 by enacting the rotating and/or pivoting of the bottomed cylindrical surface 16. In addition, for repeated use of the pivoting bottomed cylindrical surface 16, the SEE 12 and calibration tool 10 may be sterilized between uses to ensure consistency and safety of the calibration tool 10.

FIGS. 8(a)-8(h) portray various calibration charts, which may be utilized in an exemplary calibration tool, according to one or more embodiment of the subject disclosure. The various examples of calibration charts 22 provided in FIGS. 8(a) through 8(h) may be used independently or in combination in the calibration tool 10. As stated prior, calibration can be accomplished by scanning a calibration chart 22 found at the distal end 14 of the calibration tool 10. The chart 22 can be a combination of various charts for a single chart to allow for various calibrations. Multiple calibration tools 10 with different charts 22 can be used to perform multiple individual calibrations of a single SEE 12. Forward view SEE's visualize calibration charts 22 at the distal end 14 of the calibration tool 10, while side-view SEE's will visualize calibration charts 22 on the cylindrical body 18 of the calibration tool 10. Various calibration charts 22 may include a color wheel, gradients, stepped chart, variations thereof, combinations of charts, and alternatives thereof.

By way of example, FIG. 9(a) illustrates a forward view SEE 12 visualizing calibration charts 22 at the distal end 14 of the calibration tool 10. FIG. 9(b) denotes a side-view SEE 12 which is configured to visualize calibration charts 22 on the cylindrical body 18 of the calibration tool 10. Alternatively, combinations of side-view and forward view SEE's may merit a calibration tool 10 having both side-view and forward view calibration charts.

FIGS. 10(a)-10(c) provide an exemplary calibration tool, utilizing multiple stages of calibration, according to one or more embodiment of the subject disclosure. As provided in FIGS. 10(a) through 10(c), a calibration tool 10, may incorporate one or more intermediate surface(s) 30 configured in the cylindrical calibration tool 10, wherein each intermediate surface 30 in situated about perpendicular to the cylindrical body 18 of the calibration tool 10, with each intermediate surface 30 having one or more calibration chart(s) 22 for calibrating the SEE 12. Each intermediate surface 30 may be configured to allow the SEE 12 to pierce through the intermediate surface 30 by forcibly urging the calibration tool 10 parallel to and towards the SEE 12, thus advancing the SEE 12 to the following intermediate surface 30 and/or bottomed cylindrical surface 16. In one embodiment, the one or more intermediate surface(s) 30 may be capable of being rotated and/or pivoted. The rotating and/or pivoting is configured to allow the SEE 12 tip 24 to advance beyond and through the calibration tool 10 without damaging the intermediate surface 30. In various embodiments, the rotating and/or pivoting intermediate surface 30 may consist of a shutter-type element, one or more pivot attachments, or derivatives thereof. As seen in FIGS. 10(a) through 10(c), calibration is accomplished with the calibration tool 10 configured on the SEE 12, wherein upon completion of calibration, the calibration tool 10 may be urged parallel to and towards the SEE 12, enacting the rotating and/or pivoting of the intermediate surface 30, and exposing the SEE 12 tip 24 to a secondary and/or tertiary intermediate surface 30 for additional calibration. Upon completion of all stages of calibration conducted by each intermediate surface 30 and bottomed cylindrical surface 16, the SEE 12 is now properly calibrated for use by the end user. Each intermediate surface 30 may have one or more calibration chart(s) 22 for calibrating the SEE 12.

In yet another embodiment of the calibration tool 10, illustrated in FIG. 11, a SEE 12 probe employs an exemplary calibration tool 10 having multiple calibration wells, according to one or more embodiment of the subject disclosure. Each well 32 contains one or more calibration chart(s) 22 for calibrating the SEE 12. Alternatively, FIGS. 12 and 13 depicts a calibration tool 10, wherein a single well 32 in employed containing a slider 34 configured with multiple slots 36, each having a calibration chart 22. After calibration with a first calibration chart 22 in a first slot 36(a) is performed, the slider 34 is positioned for calibration of additional calibration charts in additional slots 36(b), 36(c) and 36(d). It is contemplated that additional calibration charts may be incorporated into each slot 36, as well as the use of additional slots 36 in the slider 34. Although longitudinal (FIG. 12) and rotating (FIG. 13) slider 34 configurations have been illustrated, it is contemplated herein that any appropriate and alternative configuration for a slider is within the scope of the present disclosure.

Figure 14A:
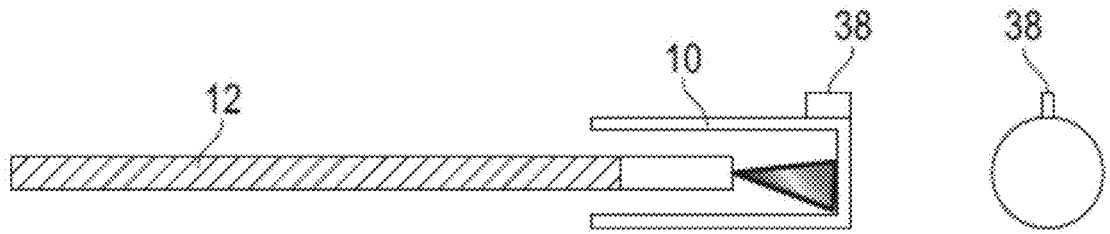
FIGS. 14(a) and 14(b) provide exemplary calibration tools, according to one or more embodiment of the subject disclosure.
Figure 14B:
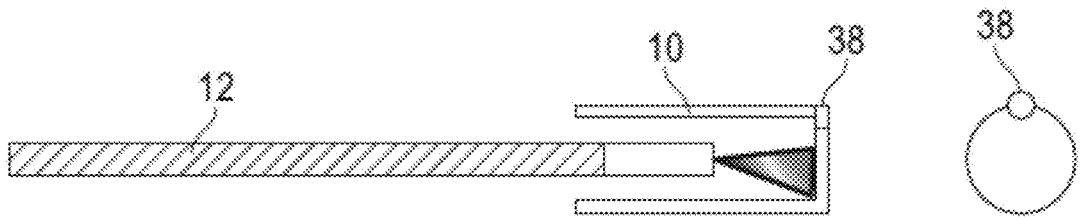
Figure 15:
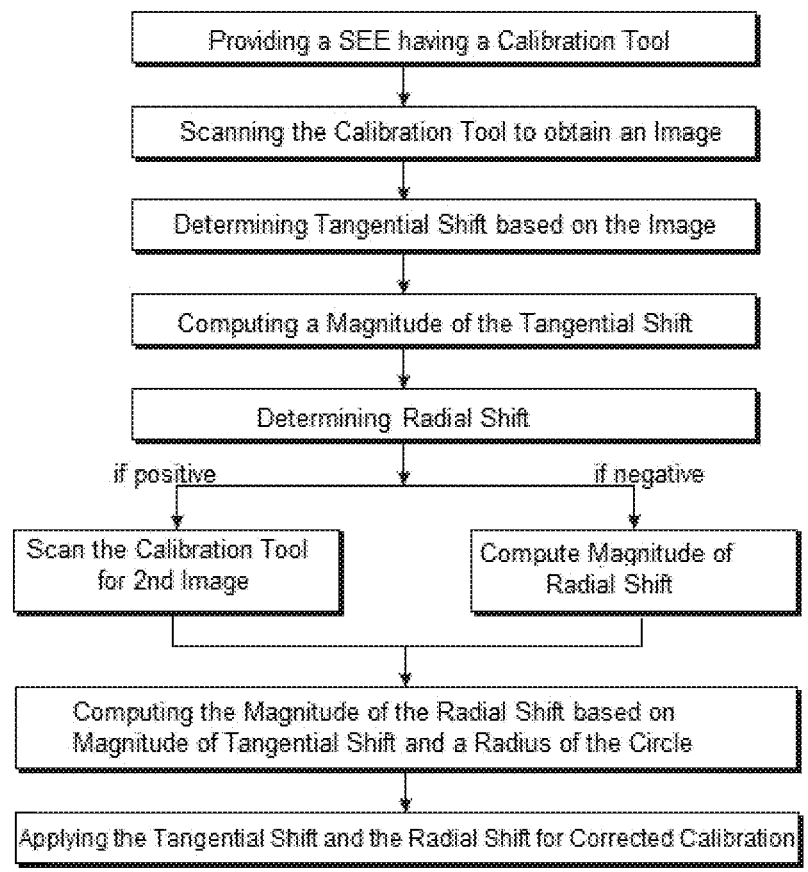
FIG. 15 is a flow chart providing a method for calibrating a SEE probe, according to one or more embodiment of the subject disclosure.

As provided in FIGS. 14(a) and 14(b), the calibration tool 10 may incorporate a visual indicator 38 for identifying the imaging orientation of the calibration tool 10, and associated SEE, when attached to the calibration tool 10. Through label markings or design features, the calibration tool 10 is used to designate SEE 12 view orientations such as 'top' or 'upright' so that the user can easily identify how to hold and manipulate the SEE 12.

Calibration for SEE

Below are various methods for calibration and/or correction of distortion for a SEE, which would be used in conjunction with the subject calibration tool, disclosed herein. A first reference pattern having a plurality of radial lines is scanned with an SEE spectral line to obtain a first image. A sign of a tangential shift of the spectral line is determined based on a slope of at least one of the radial lines of the first image in a polar coordinate. A magnitude of the tangential shift is computed based on at least one of the radial lines of the first image in either a polar coordinate or a Cartesian coordinate. A sign of a radial shift of the spectral line is determined based on whether the slope has a turning point or not. A magnitude of the radial shift is determined by measuring a location of the turning point if the radial shift is determined to be negative. A second reference pattern comprising at least a circle is scanned to obtain a second image if the radial shift is determined to be positive. The magnitude of the radial shift is computed based on the magnitude of the tangential shift and a radius of the circle. The tangential shift and the radial shift are then applied for correcting distortion.

By way of example, the step of computing the magnitude of the tangential shift comprises determining a shift of the radial line of the first image from an original position in the Cartesian coordinate. Alternatively, the step of computing the magnitude of the tangential shift may comprise selecting at least three radial lines with the spectral line that are equally spaced from each other with an angle and each intersecting with the spectral line at an intersection point and computing the magnitude of the tangential shift based on the angle, a first distance between the intersecting points of a first and a second of the at least three radial lines, and a second distance between the intersecting points of the second and a third of the intersecting points.

The step of computing a magnitude of the radial shift may further include measuring the location of the turning point by determining where a second derivative of the radial line is zero if the radial shift is determined to be negative. The method may include, wherein when the sign of the radius shift is positive, the magnitude of the radial shift is computed by the relations:

$$R_r = \sqrt{R_0^2 - R_t^2} - d$$

where $R_r$ is the radial shift, $R_t$ is the tangential shift, $R_o$ is the radius of the circle, and $d$ is the distance between the circle and a target radius. When the sign of the radius shift is negative, the magnitude of the radial shift is computed by the relations:

$$R_r = d - \sqrt{R_0^2 - R_t^2}$$

where $R_r$ is the radial shift, $R_t$ is the tangential shift, $R_o$ is the radius of the circle, and $d$ is the distance between the circle and a target radius.

The step of applying the tangential shift and the radial shift for correcting distortion further comprises applying the tangential shift and the radial shift to determine actual location (x', y') of the radial lines represented by:

$$x' = \rho \cos\theta - R_t \sin\theta + R_r \cos\theta$$

$$y' = \rho \sin\theta + R_t \cos\theta + R_r \sin\theta$$

where $\rho$ is pixel index along the SEE spectral line, $\theta$ is rotation angle of the SEE spectral line.

An additional method for correcting distortion of a spectrally encoded endoscopy (SEE) image includes the following steps. A first reference pattern comprising a plurality of radial lines is scanned with an SEE spectral line to obtain a first image. A sign of a tangential shift of the spectral line is determined based on a slope of at least one of the radial lines of the first image in a polar coordinate. A second reference pattern comprising at least two concentric circles is scanned with the SEE spectral line to obtain a second image, the two concentric circles having a first radius and a second radius, respectively. The magnitude of the tangential shift and a magnitude of a radial shift of the spectral line are scanned by measuring locations of the spectral line corresponding to the two concentric circles in the polar coordinate. The tangential shift and the radial shift are applied for correcting distortion.

The step of computing the magnitude of the tangential shift may comprise determining a shift of the radial line of the first image from an original position in the Cartesian coordinate. The radial shift may be calculated based on the relationship:

$$R_r = \frac{R_2^2 - R_1^2}{2(d_2 - d_1)} - \frac{d_1 + d_2}{2},$$

and the tangential shift is calculated based on the relationship:

$$R_t^2 = \frac{R_2^2 + R_1^2}{2} - \frac{(R_2^2 - R_1^2)^2}{4(d_2 - d_1)^2} - \frac{(d_2 - d_1)^2}{4}.$$

The step of applying the tangential shift and the radial shift for correcting distortion further comprises applying the tangential shift and the radial shift to determine actual location (x', y') of the radial lines represented by:

$$x' = \rho \cos\theta - R_t \sin\theta + R_r \cos\theta$$

$$y' = \rho \sin\theta + R_t \cos\theta + R_r \sin\theta$$

where $\rho$ is pixel index along the SEE spectral line, $\theta$ is rotation angle of the SEE spectral line.

In another embodiment, a first reference pattern comprising a plurality of radial lines is scanned with an SEE spectral line to obtain a first image. A sign of a tangential shift of the spectral line is determined based on a slope of at least one of the radial lines of the first image in a polar coordinate. A magnitude of the tangential shift is determined based on a shift of at least one of the plurality of the radial lines on a Cartesian coordinate or based on at least three angularly equally radial lines included in the plurality of radial lines scanned by the SEE spectral line. The magnitude of the tangential shift is computed based on the a shift of at least one of the radial lines or based on at least three angularly equally spaced radial lines included in the plurality of radial lines. A second reference pattern comprising at least two concentric circles is scanned with the SEE spectral line to obtain a second image, the two concentric circles having a first radius and a second radius, respectively. A ratio of the second radius to the first radius is provided. A radial shift of the spectral lines is computed based on the tangential shift and the ratio; and the tangential shift and the radial shift are applied for correcting distortion.

The step of computing the magnitude of the tangential shift may comprise determining a shift of the radial line of the first image from an original position in the Cartesian coordinate. The step of computing the magnitude of the tangential shift may also comprise selecting at least three radial lines that are equally spaced from each other with an angle and each intersecting with the spectral line at an intersection point and computing the magnitude of the tangential shift based on the angle, a first distance between the intersecting points of a first and a second of the at least three radial lines, and a second distance between the intersecting points of the second and a third of the intersecting points.

The radial shift is calculated based on the relationship of:

$$R_r = \frac{-(d_1 \times k^2 - d_2) \pm \sqrt{k^2 \times (d_2 - d_1)^2 - R_t^2(k^2 - 1)^2}}{k^2 - 1}$$

where $k$ is the ratio of the second radius to the first radius. The step of applying the tangential shift and the radial shift for correcting distortion further comprises applying the tangential shift and the radial shift to determine actual location (x', y') of the radial lines represented by:

$$x' = \rho \cos\theta - R_t \sin\theta + R_r \cos\theta$$

$$y' = \rho \sin\theta + R_t \cos\theta + R_r \sin\theta$$

where $\rho$ is pixel index along the SEE spectral line, $\theta$ is rotation angle of the SEE spectral line.

Another method for correcting distortion of a spectrally encoded endoscopy (SEE) image, includes, a first reference pattern comprising a plurality of radial lines is scanned with an SEE spectral line to obtain a first image. A sign of a tangential shift of the spectral line is determined based on a slope of at least one of the radial lines of the first image in a polar coordinate. A magnitude of the tangential shift is determined based on a shift of at least one of the plurality of the radial lines on a Cartesian coordinate or based on at least three angularly equally radial lines included in the plurality of radial lines scanned by the SEE spectral line. A second reference pattern comprising at least two concentric circles is scanned with the SEE spectral line to obtain a second image, the two concentric circles having a first radius and a second radius, respectively. A ratio of the second radius to the first radius is provided. Two possible values of the magnitude of a radial shift of the spectral lines are computed based on the tangential shift and the ratio. One of the possible values is selected to calculate pixel coordinate of the radial lines imaged by the spectral line. The tangential shift and the radial shift are applied for correcting distortion. The other of the possible values of the magnitude of the radial shift is selected if the distortion is not corrected by the first possible value.

The invention claimed is:

1. A method for calibrating a rotating SEE, the method comprising:
    providing a calibration apparatus comprising:
        a body configured to encompass at least a portion of a SEE;
        a bottomed surface affixed to a distal end of the body; and
        a calibration chart configured on an inside wall portion of the apparatus,
        wherein the apparatus has an open end, opposite the bottomed surface, wherein the open end is configured to receive the at least a portion of the SEE, and the SEE is a rotating SEE,
    scanning the calibration chart with a SEE spectral line to obtain an image;
    determining a sign of a tangential shift of the spectral line based on a slope of at least one of the radial lines of the first image in a polar coordinate;
    computing a magnitude of the tangential shift based on at least one of the radial lines of the first image in either a polar coordinate or a Cartesian coordinate;
    determining a sign of a radial shift of the spectral line based on whether the slope has a turning point or not;
    computing a magnitude of the radial shift by measuring a location of the turning point if the radial shift is determined to be negative;
    scanning the calibration chart with the SEE spectral line to obtain a second image if the radial shift is determined to be positive;
    computing the magnitude of the radial shift based on the magnitude of the tangential shift and a radius of the circle; and
    applying the tangential shift and the radial shift for a corrected calibration.

2. The method of claim 1, wherein the calibration apparatus further comprising an attachment element configured to rigidly and removably attach the apparatus to the SEE.

3. The method of claim 1, wherein the calibration apparatus is configured to further extend onto a sheath of the SEE.

4. The method of claim 1, wherein the calibration apparatus is configured for repeated attachment and removal from the at least a portion of the SEE.

5. The method of claim 1, wherein the calibration chart of the calibration apparatus is positioned at a predetermined distance from the SEE.

6. The method of claim 1, wherein the bottomed surface of the calibration apparatus is configured to be ruptured by the SEE, allowing the SEE to protrude through the bottomed surface of the apparatus.

7. The method of claim 1, wherein the calibration apparatus further comprising a second calibration chart configured on an inside wall portion of the apparatus.

8. The method of claim 1, wherein the bottomed surface of the calibration apparatus is configured to be rotatable or pivotable, allowing for rearrangement of the bottomed surface with respect to the SEE.

9. The method of claim 1, wherein the calibration chart in the body has a diameter larger than a diameter of the SEE.

* * * * *